(12) United States Patent
Hsieh

(10) Patent No.: US 9,592,407 B2
(45) Date of Patent: Mar. 14, 2017

(54) PHARMACEUTICAL COMPOSITION AND USES THEREOF

(71) Applicants: CHANG GUNG MEMORIAL HOSPITAL, LINKOU, Gueishan Township, Taoyuan County (TW); Thomas Hsieh, Taipei (TW)

(72) Inventor: Sen-yung Hsieh, Gueishan Township (TW)

(73) Assignees: CHANG GUNG MEMORIAL HOSPITAL, Taoyuan (TW); LINKOU & HSIEH, THOMAS, Taipei (TW)

( * ) Notice: Subject to any disclaimer, the term of this patent is extended or adjusted under 35 U.S.C. 154(b) by 0 days.

(21) Appl. No.: 14/427,772

(22) PCT Filed: Sep. 13, 2013

(86) PCT No.: PCT/US2013/059723
§ 371 (c)(1),
(2) Date: Mar. 12, 2015

(87) PCT Pub. No.: WO2014/043510
PCT Pub. Date: Mar. 20, 2014

(65) Prior Publication Data
US 2015/0224334 A1    Aug. 13, 2015

Related U.S. Application Data

(60) Provisional application No. 61/700,756, filed on Sep. 13, 2012.

(51) Int. Cl.
*A61N 5/06* (2006.01)
*A61K 45/06* (2006.01)
(Continued)

(52) U.S. Cl.
CPC ............ *A61N 5/062* (2013.01); *A61K 31/352* (2013.01); *A61K 31/407* (2013.01);
(Continued)

(58) Field of Classification Search
None
See application file for complete search history.

(56) References Cited

U.S. PATENT DOCUMENTS 4,938,949 A    7/1990   Borch et al.
8,063,089 B2*  11/2011  Mahadevan ......... C07D 209/20
                                                        514/394

FOREIGN PATENT DOCUMENTS

WO    2012/112626    8/2012

OTHER PUBLICATIONS

"General Principles" in Goodman & Gilman's Manual of Pharmacology and Therapeutics, 11th ed. c2006, McGraw Hill Professional. New York : McGraw-Hill Medical. 2008, pp. 1-25.*
(Continued)

*Primary Examiner* — Karl J Puttlitz
(74) *Attorney, Agent, or Firm* — Leason Ellis LLP

(57) ABSTRACT

Pharmaceutical compositions containing a combination of NPM inhibitor and anti-cancer agent are disclosed. Methods of inhibiting or reducing the growth of cancer cells in a subject, by administering an effective amount of nucleophosmin (NPM) inhibitor and one or more anticancer agents, whereby the symptoms and signs of cancer in the subject are reduced are also provided.

3 Claims, 6 Drawing Sheets

(51) Int. Cl.
  A61K 31/352   (2006.01)
  A61K 31/44    (2006.01)
  A61K 31/517   (2006.01)
  A61K 31/704   (2006.01)
  A61K 31/713   (2006.01)
  A61K 31/407   (2006.01)
  A61K 31/4184  (2006.01)
  A61K 33/24    (2006.01)
  C12N 15/113   (2010.01)

(52) U.S. Cl.
  CPC .......... *A61K 31/4184* (2013.01); *A61K 31/44* (2013.01); *A61K 31/517* (2013.01); *A61K 31/704* (2013.01); *A61K 31/713* (2013.01); *A61K 33/24* (2013.01); *A61K 45/06* (2013.01); *C12N 15/113* (2013.01); *A61N 2005/0661* (2013.01); *C12N 2310/14* (2013.01); *C12N 2320/31* (2013.01)

(56) References Cited

OTHER PUBLICATIONS

"Chemotherapy of Neoplastic Diseases" in Goodman & Gilman's Manual of Pharmacology and Therapeutics, 11th ed. c2006, McGraw Hill Professional. New York : McGraw-Hill Medical. 2008, pp. 853-861.*

Shu et al., Basic & Clinical Pharmacology & Toxicology (2008), 103(6), 530-537.*

"International Search Report and Written Opinion of the International Searching Authority", Patent Cooperation Treaty International Searching Authority (Jan. 7, 2014), PCT/US2013/059723, 9 pgs.

Chou, "Theoretical basis, experimental design, and computerized simulation of synergism and antagonism in drug combination studies", Pharmacol Rev (Sep. 2006), 58(3):621-81.

Hsieh; et al., "Identifying apoptosis-evasion proteins/pathways in human hepatoma cells via induction of cellular hormesis by UV irradiation", J Proteome Res (Aug. 2009), 8(8):3977-86.

Perea; et al., "Antitumor effect of a novel proapoptotic peptide that impairs the phosphorylation by the protein kinase 2 (casein kinase 2)", Cancer Res (Oct. 2004), 64(19):7127-9.

Prasad; et al., "Gambogic Acid Inhibits STAT3 Phoshorylation Through Activation of Protein Tyrosine Phosphatase SHP-1: Potential Role in Proliferation and Apoptosis", Cancer Prevention Research (Jul. 2011), 4(7):1084-94.

Sekhar; et al., "The novel chemical entity YTR107 inhibits recruitment of nucleophosmin to sites of DNA damage, suppressing repair of DNA double-strand breaks and enhancing radiosensitization", Clin Cancer Res (Oct. 2011), 17 (20):6490-9.

* cited by examiner

SEQUENCE LISTING

```
<160> NUMBER OF SEQ ID NOS: 5

<210> SEQ ID NO 1
<211> LENGTH: 294
<212> TYPE: PRT
<213> ORGANISM: Homo sapiens

<400> SEQUENCE: 1

Met Glu Asp Ser Met Asp Met Asp Met Ser Pro Leu Arg Pro Gln Asn
1               5                   10                  15

Tyr Leu Phe Gly Cys Glu Leu Lys Ala Asp Lys Asp Tyr His Phe Lys
            20                  25                  30

Val Asp Asn Asp Glu Asn Glu His Gln Leu Ser Leu Arg Thr Val Ser
        35                  40                  45

Leu Gly Ala Gly Ala Lys Asp Glu Leu His Ile Val Glu Ala Glu Ala
    50                  55                  60

Met Asn Tyr Glu Gly Ser Pro Ile Lys Val Thr Leu Ala Thr Leu Lys
65                  70                  75                  80

Met Ser Val Gln Pro Thr Val Ser Leu Gly Gly Phe Glu Ile Thr Pro
                85                  90                  95

Pro Val Val Leu Arg Leu Lys Cys Gly Ser Gly Pro Val His Ile Ser
            100                 105                 110

Gly Gln His Leu Val Ala Val Glu Glu Asp Ala Glu Ser Glu Asp Glu
        115                 120                 125

Glu Glu Glu Asp Val Lys Leu Leu Ser Ile Ser Gly Lys Arg Ser Ala
    130                 135                 140

Pro Gly Gly Gly Ser Lys Val Pro Gln Lys Lys Val Lys Leu Ala Ala
145                 150                 155                 160

Asp Glu Asp Asp Asp Asp Asp Glu Glu Asp Asp Asp Glu Asp Asp
                165                 170                 175

Asp Asp Asp Asp Phe Asp Asp Glu Glu Ala Glu Glu Lys Ala Pro Val
            180                 185                 190
```

```
Lys Lys Ser Ile Arg Asp Thr Pro Ala Lys Asn Ala Gln Lys Ser Asn
        195                 200                 205

Gln Asn Gly Lys Asp Ser Lys Pro Ser Ser Thr Pro Arg Ser Lys Gly
    210                 215                 220

Gln Glu Ser Phe Lys Lys Gln Glu Lys Thr Pro Lys Thr Pro Lys Gly
225                 230                 235                 240

Pro Ser Ser Val Glu Asp Ile Lys Ala Lys Met Gln Ala Ser Ile Glu
                245                 250                 255

Lys Gly Gly Ser Leu Pro Lys Val Glu Ala Lys Phe Ile Asn Tyr Val
                260                 265                 270

Lys Asn Cys Phe Arg Met Thr Asp Gln Glu Ala Ile Gln Asp Leu Trp
        275                 280                 285

Gln Trp Arg Lys Ser Leu
    290

<210> SEQ ID NO 2
<211> LENGTH: 21
<212> TYPE: DNA
<213> ORGANISM: Artificial sequence
<220> FEATURE:
<223> OTHER INFORMATION: siRNA targeting NPM; siNPM s9676 sense strand

<400> SEQUENCE: 2
cgacaaagau uaucacuuut t                                              21

<210> SEQ ID NO 3
<211> LENGTH: 20
<212> TYPE: DNA
<213> ORGANISM: Artificial Sequence
<220> FEATURE:
<223> OTHER INFORMATION: siRNA targeting NPM, siNPM s9676 antisense
      strand

<400> SEQUENCE: 3
aaaggauaau cuuugucggc                                                20

<210> SEQ ID NO 4
<211> LENGTH: 21
<212> TYPE: DNA
<213> ORGANISM: Artificial Sequence
<220> FEATURE:
<223> OTHER INFORMATION: siRNA targeting NPM, siNPM s9677 sense strand

<400> SEQUENCE: 4
gcaaugaauu acgaaggcat t                                              21

<210> SEQ ID NO 5
<211> LENGTH: 21
<212> TYPE: DNA
<213> ORGANISM: Artificial Sequence
<220> FEATURE:
<223> OTHER INFORMATION: siRNA targeting NPM, siNPM s9677 antisense
      strand

<400> SEQUENCE: 5
ugccuucgua auucauugcc t                                              21
```

PHARMACEUTICAL COMPOSITION AND USES THEREOF

CROSS-REFERENCE TO RELATED APPLICATIONS

This application is a national stage under 35 U.S.C. 371 based on and claiming the benefit of International Application PCT/US2013/059723, filed on Sep. 13, 2013, which claims priority from U.S. Provisional Application No. 61/700,756, filed Sep. 13, 2012, the entire contents of each of which are incorporated herein by reference.

BACKGROUND OF THE INVENTION

Nucleophosmin (NPM) is a highly conserved phosphoprotein mainly located in nucleoli, and shuttles between the nucleoli and cytoplasm during the cell cycle. It has been implicated in regulation of ribosome biogenesis, centrosome duplication, genome stability and apoptosis.

Cancer remains a major public health problem worldwide. It profoundly affects more than 1 million people in the U.S. diagnosed each year, as well as their families and friends. Despite the advance in chemotherapy over the last 50 years, the medical community is still faced with the challenge for treating many types of cancer. Accordingly, there is still a need for a more effective and safe cancer treatment. The present invention addresses this need.

BRIEF SUMMARY OF THE INVENTION

Some embodiments provide a pharmaceutical composition comprising one or more NPM inhibitors and one or more anti-cancer agents. Advantageously, this combination has additive or synergistic effects on cancer inhibition.

Some embodiments provide methods for reducing or inhibiting cancer growth, comprising administering an effective amount of NPM inhibitor and an effective amount of anti-cancer agent to a subject in need thereof to thereby reduce or inhibit cancer growth.

BRIEF DESCRIPTION OF THE DRAWINGS

FIG. 6A illustrates the expression of NPM and BAX in the cytosol and the mitochondria of Mahlavu liver cancer cells following UV irradiation with or without transfected siRNA targeting NPM (NPM) or siRNA with scrambled sequences (NS). FIG. 6B illustrates the effect of siNPM and siNS on BAX dimmers (indicated with an asterisk) and BAX oligomers (twin-asterisk) in the mitochondria or the nuclei.

DETAILED DESCRIPTION OF THE INVENTION

Definition

Figure 1:
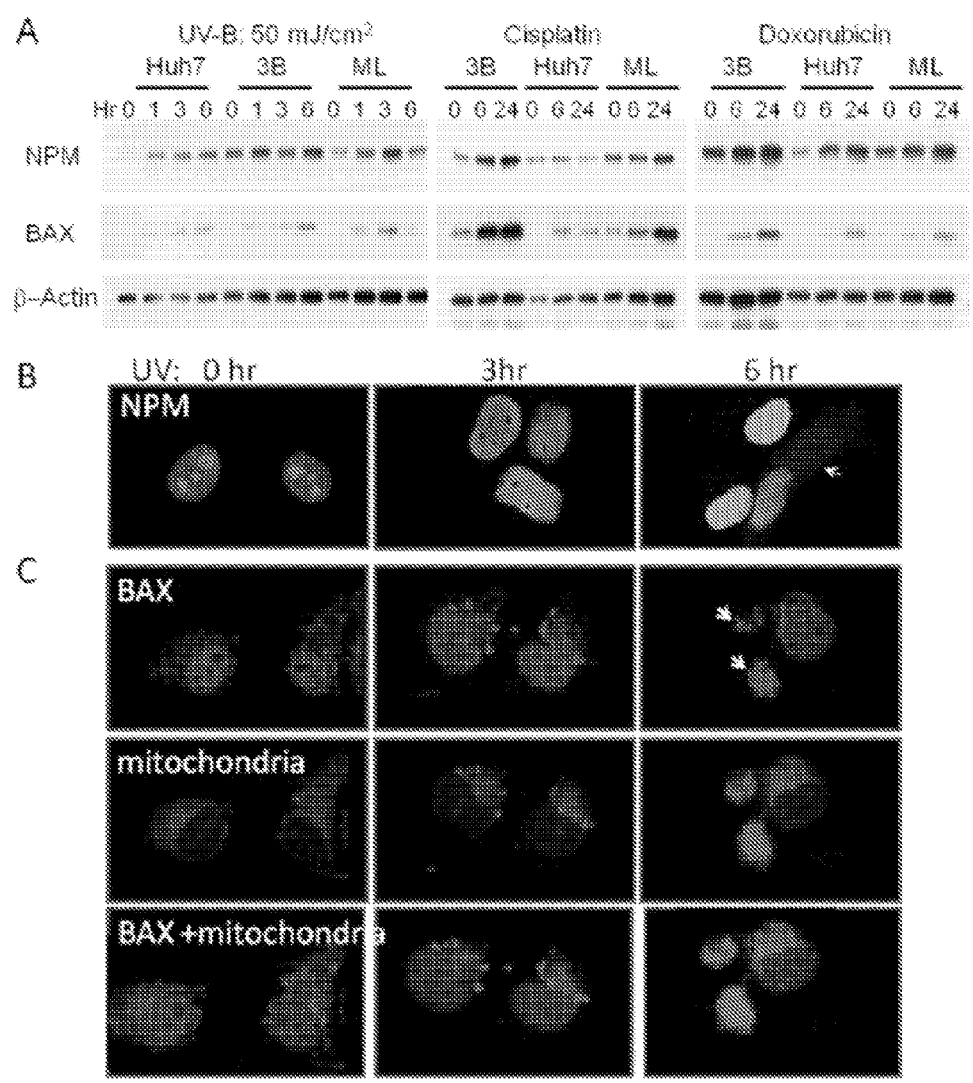
FIG. 1A shows expression of NPM and BCL2-associated X protein (BAX) in liver cancer cells following exposure to UV-B, cisplatin, or doxorubicin.
FIG. 1B shows subcellular distribution of NPM before UV-B irradiation (left panel), 3 hr after UV-B irradiation (middle panel), and 6 hr after (right panel) UVB irradiation. A subset of NPM was translocated to cytoplasm 6 hr after UV irradiation (indicated by an arrow in the right panel).
FIG. 1C shows subcellular distribution of BAX (upper panel), mitochondria (middle panel), and BAX and mitochondria (lower panel).

As employed above and throughout the disclosure, the following terms, unless otherwise indicated, shall be understood to have the following meanings.

The terms "invention," "the invention," "this invention" and "the present invention" used in this patent are intended to refer broadly to all of the subject matter of this patent and the patent claims below. Statements containing these terms should be understood not to limit the subject matter described herein or to limit the meaning or scope of the patent claims below. Embodiments of the invention covered by this patent are defined by the claims below, not in this specification. The specification is not intended to identify essential features of the claimed subject matter, nor is any portion of the specification to be used in isolation to determine the scope of the claimed subject matter. Claimed subject matter is to be understood by reference to appropriate portions of the entire specification, including all text and drawings and each claim.

As used herein, the singular forms "a," "an," and "the" include the plural reference unless the context clearly indicates otherwise.

An "effective amount," as used herein, includes a dose of an NPM inhibitor or anti-cancer agent that is sufficient to reduce the symptoms and/or signs of cancer.

The term "treating," "treated," or "treatment" as used herein includes preventative (e.g. prophylactic), palliative, and curative uses or results.

The term "inhibiting" and "suppressing" includes slowing or stopping the growth of.

The term "subject" includes a vertebrate having or at risk of developing cancer. Preferably, the subject is a warm-blooded animal, including mammals, preferably humans.

The term "pharmaceutically acceptable salts" of an acidic therapeutic agent of the pharmaceutical composition are salts formed with bases, namely base addition salts such as alkali and alkaline earth metal salts, such as sodium, lithium, potassium, calcium, magnesium, as well as 4 ammonium salts, such as ammonium, trimethyl-ammonium, diethylammonium, and tris-(hydroxymethyl)-methyl-ammonium salts. Similarly, acid addition salts, such as of mineral acids, organic carboxylic and organic sulfonic acids, e.g., hydrochloric acid, methanesulfonic acid, maleic acid, are also possible provided to a basic therapeutic agent with a constitute such as pyridyl, as part of the structure.

Pharmaceutical Composition

Some embodiments of the present invention is directed to pharmaceutical compositions for reducing or inhibiting cancer cell growth. The pharmaceutical compositions comprising a combination of at least one NPM inhibitors and at least one anti-cancer agents. The NPM inhibitor and the anti-cancer agent may produce additive or synergistic effects.

NPM Inhibitor

An NPM inhibitor is any agent which reduces or slows the expression of NPM, and/or reduces NPM's activity. In one embodiment, the NPM inhibitor is (Z)-5-((N-benzyl-1H-indol-3-yl)methylene) imidazolidine-2,4-dione derivative or a pharmaceutically acceptable salt thereof. In another embodiment, the NPM inhibitor is 5-((N-benzyl-1H-indol-3-yl)methylene) pyrimidine-2,4,6(1H,3H,5H)trione derivative or a pharmaceutically acceptable salt thereof that incorporate a variety of substituents in both the indole and N-benzyl moieties, which are disclosed in Sekhar et al, "The Novel Chemical Entity YTR107 Inhibits Recruitment of Nucleophosmin to Sites of DNA Damage, Suppressing Repair of DNA Double-Strand Breaks and Enhancing Radiosensitization" *Clin Cancer Res* 2011; 17:6490-6499. In another embodiment, the NPM inhibitor is NSC 348884 or a pharmaceutically acceptable salt thereof, which is disclosed in U.S. Pat. No. 8,063,089 and is incorporated herein by reference in its entirety. In another embodiment, the NPM inhibitor is CIGB-300, a cyclic peptide that impairs CK2 phosphorylation after intracellular delivery. The synthesis of CIGB-300 was described in Perea et al "Antitumor effect of a novel proapoptotic peptide that impairs the phosphorylation by the protein kinase 2 (casein kinase 2). Cancer Res 2004; 64:7127-9" and is incorporated herein by reference in its entirety. In another embodiment, the NPM inhibitor is Gambogic acid or a pharmaceutically acceptable salt.

In some embodiments, the NPM inhibitor is a small interfering RNA (e.g., siRNA, short interfering RNA or silencing RNA) targeting NPM RNA transcription to decrease the expression of NPM. In other embodiments, the NPM inhibitor is a biosynthetic precursor of a NPM-targeted small interfering RNA. Small interfering RNAs are typically short double-stranded RNA species with phosphorylated 5' ends and hydroxylated 3' ends with two or more overhanging nucleotides. In some embodiments, the NPM inhibitor is an siRNA comprising s9676 (SEQ ID NOs: 2 and 3), wherein SEQ ID NO: 2 represents the sense strand and SEQ ID NO: 3 represents the antisense strand. In some embodiments, the NPM inhibitor is an siRNA comprising s9677 (SEQ ID NOs: 4 and 5), wherein SEQ ID NO: 4 represents the sense strand and SEQ ID NO: 5 represents the antisense strand. In some embodiments, the NPM inhibitor is any RNA species such as but not limited to, microRNA (miRNA), short hairpin RNA, endoribonuclease-prepared siRNA (esiRNA), natural antisense short interfering RNA (natsiRNA), wherein the RNA species targets the NPM RNA transcription to decrease the expression of NPM.

In an embodiment, the NPM inhibitor is 5-((N-benzyl-1H-indol-3-yl)methylene)pyrimidine-2,4,6(1H,3H,5H)trione (denoted as YTR107, See Formula (I)).

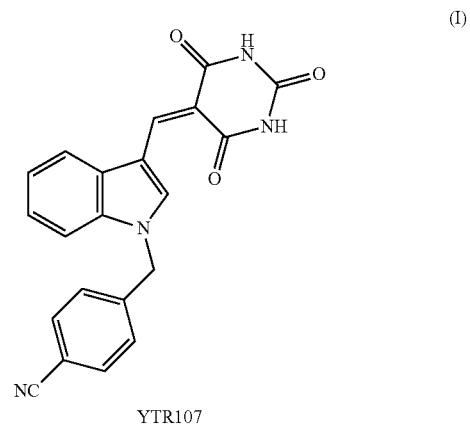

YTR107

Anti-Cancer Agent

The anti-cancer agent includes conventional chemotherapeutic agent, target cancer therapy or radiation therapy.

The conventional chemotherapeutic agent comprises anthracycline antibiotic, DNA synthesis inhibitor, alkylating agent, antifolate agent, metabolic inhibitor or combination thereof.

Examples of anthracycline antibiotic include, but are not limited to, doxorubicin, Epirubicin, Mitoxantrone and the like.

Examples of DNA synthesis inhibitor include, but are not limited to, mitomycin C, 5FU(5-Fluorouracil), Capecitabine, Irinotecan hydrochloride, thymitaq and the like.

Examples of alkylating agent include, but are not limited to, cisplatin, carboplatin, oxaliplatin, mitoxantrone and the like.

Examples of metabolic inhibitor include, but are not limited to, etoposide, rottlerin and the like.

Examples of antifolate agent include, but are not limited to, Nolatrexed and the like.

The target cancer therapy are medications which inhibit the growth of cancer cells by interfering with specific targeted molecules needed for carcinogenesis and cancer growth, rather than by simply interfering with rapidly dividing cells (e.g., with conventional chemotherapeutic agent). In some embodiments, the target cancer therapy comprises kinase inhibitor, angiogenesis inhibitor, epidermal growth factor receptor (EGFR) inhibitor, HER2/neu receptor or the combination thereof.

Examples of kinase inhibitor include, but are not limited to, gefitinib, lapatinib, sorefenib, sunitinib, erlotinib, ABT-869, ARQ 197 and the like.

Examples of angiogenesis inhibitor include, but are not limited to, Avastin, Brivanib, Bevacizumab, Ramucirumab and the like.

Examples of EGFR inhibitor include, but are not limited to, Gefitinib, Cetuximab and the like.

Examples of HER2/neu receptor include, but are not limited to, Trastuzumab, Lapatinib, or the like.

Anti-cancer agents are known for side effects, such as weight loss, loss of hair, anemia, neutropenia and thrombocytopenia. These side effects may be overcome by administering lower dosage of anti-cancer agent in combination with one or more NPM inhibitors to achieve the desired therapeutic effect. The observed synergistic or additive effect of a pharmaceutical composition comprising a combination of a NPM inhibitor and an anti-cancer agent (e.g., Cisplatin) may afford effective inhibition or reduction of cancer cell growth wherein one or even all of the lower dosages of the anti-cancer agents would not be sufficient to have a therapeutic effect when the respective anti-cancer agent is used in monotherapy.

The pharmaceutical compositions to be administered according to the methods of some embodiments provided herein can be readily formulated with, prepared with, or administered with, a pharmaceutically acceptable carrier. Such pharmaceutical compositions may be prepared by various techniques. Such techniques include bringing into association active components (such as an NPM inhibitor) of the pharmaceutical compositions and a pharmaceutically acceptable carrier. In one embodiment, pharmaceutical compositions are prepared by uniformly and intimately bringing into association active components of the pharmaceutical compositions with liquid carriers, with solid carriers, or with both. Liquid carriers include, but are not limited to, aqueous formulations, non-aqueous formulations, or both. Solid carriers include, but are not limited to, biological carriers, chemical carriers, or both.

The pharmaceutical compositions are administered in an aqueous suspension, an oil emulsion, water in oil emulsion and water-in-oil-in-water emulsion, and in carriers including, but not limited to, creams, gels, liposomes (neutral, anionic or cationic), lipid nanospheres or microspheres, neutral, anionic or cationic polymeric nanoparticles or microparticles, site-specific emulsions, long-residence emulsions, sticky-emulsions, micro-emulsions, nano-emulsions, microspheres, nanospheres, nanoparticles and minipumps, and with various natural or synthetic polymers that allow for sustained release of the pharmaceutical composition including anionic, neutral or cationic polysaccharides and anionic, neutral cationic polymers or copolymers, the minipumps or polymers being implanted in the vicinity of where composition delivery is required. Furthermore, the active components of the pharmaceutical compositions provided herein are useful with any one, or any combination of, carriers. These include, but are not limited to, anti-oxidants, buffers, and bacteriostatic agents, and optionally include suspending agents, thickening agents or preservatives.

For administration in a non-aqueous carrier, active components of the pharmaceutical compositions provided herein are emulsified with a mineral oil or with a neutral oil such as, but not limited to, a diglyceride, a triglyceride, a phospholipid, a lipid, an oil and mixtures thereof, wherein the oil contains an appropriate mix of polyunsaturated and saturated fatty acids. Examples include, but are not limited to, soybean oil, canola oil, palm oil, olive oil and myglyol, wherein the number of fatty acid carbons is between 12 and 22 and wherein the fatty acids can be saturated or unsaturated. Optionally, charged lipid or phospholipid is suspended in the neutral oil. A suitable phospholipid is, but is not limited to, phosphatidylserine, which targets receptors on macrophages. The pharmaceutical compositions provided herein are optionally formulated in aqueous media or as emulsions using known techniques.

The pharmaceutical compositions provided herein may optionally include active agents described elsewhere, and, optionally, other therapeutic ingredients. The carrier and other therapeutic ingredients must be acceptable in the sense of being compatible with the other ingredients of the composition and not deleterious to the recipient thereof.

The pharmaceutical compositions are administered in an amount effective to inhibit or reduce cancer cell growth. The dosage of the pharmaceutical composition administered will depend on the severity of the condition being treated, the particular formulation, and other clinical factors such as weight and the general condition of the recipient and route of administration.

Useful dosages of the pharmaceutical compositions provided herein are determined by comparing their in vitro activity, and in vivo activity in animal models. Methods for the extrapolation of effective dosages in mice, and other animals, to humans are known in the art; for example, see U.S. Pat. No. 4,938,949, which is incorporated by reference herein.

The NPM inhibitor or the anti-cancer agent can be administered at any effective amount. In some embodiments, they may be administered at a dose ranging from about 0.01 µg to about 5 g, from about 0.1 µg to about 1 g, from about 1 µg to about 500 mg, from about 10 µg to about 100 mg, from about 50 µg to about 50 mg, from about 100 µg to about 10 mg, from about 0.5 µg to about 5 µg, from about 15 µg to about 500 µg, from about 3 µg to about 1 mg, from about 7 µg to about 1 mg, from about 10 µg to about 20 µg, from 15 µg to about 1 mg, from about 15 µg to about 300 µg, from about 15 µg to about 200 µg, from about 15 µg to about 100 µg, from about 15 µg to about 60 µg, from about 15 µg to about 45 µg, from about 30 µg to about 60 µg, or from about 50 µg to about 100 µg. In certain embodiments, the NPM inhibitor or the anti-cancer agent is administered in a dose ranging from about 0.1 µg/kg bodyweight to about 200 mg/kg bodyweight, from about 1 µg/kg bodyweight to about 100 mg/kg bodyweight, from about 100 µg/kg to about 50 mg/kg bodyweight, from about 0.5 mg/kg to about 20 mg/kg bodyweight, from about 1 mg/kg to about 10 mg/kg bodyweight, from about 10 µg/kg bodyweight to about 200 µg/kg bodyweight, at least about 0.01 µg/kg bodyweight, about 0.1 µg/kg bodyweight, or at least about 0.5 µg/kg bodyweight.

In accordance with the methods provided herein, the pharmaceutical composition is delivered by any of a variety of routes including, but not limited to, injection (e.g., subcutaneous, intramuscular, intravenous, intra-arterial, intraperitoneal, intradermal); cutaneous; dermal; transdermal; oral (e.g., tablet, pill, liquid medicine, edible film strip); implanted osmotic pumps; suppository, aerosol spray, topical, intra-articular, ocular, nasal inhalation, pulmonary inhalation, impression into skin and vaginal.

The pharmaceutical composition may be administered in a single dose treatment or in multiple dose treatments, over a period of time appropriate to the condition being treated. The pharmaceutical composition may conveniently be administered at appropriate intervals, for example, once a day, twice a day, three times a day, once every second day, once every three days or once every week, over a period of at least 3 months or until the symptoms and signs of the condition resolved.

The Method of Suppressing Cancer Growth

Some embodiments of the invention is directed to methods of inhibiting or suppressing cancer growth in a subject, which comprises the administration an effective amount of at least one NPM inhibitor and at least one anti-cancer agent (as described herein) to a subject in need thereof, whereby the symptoms and/or signs of the cancer in the subject are reduced.

Figure 2:
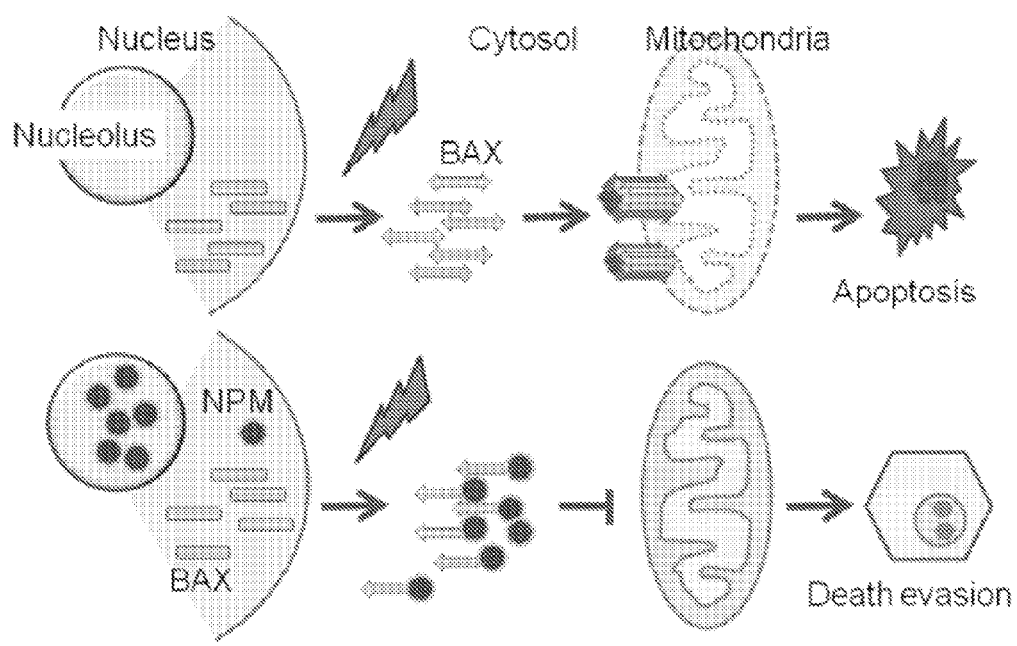
FIG. 2 illustrates schematically the intracellular apoptosis and death evasion pathways involving NPM and BAX.

Nucleophosmin or NPM (SEQ ID NO:1) is a highly conserved anti-apoptosis protein that shuffles between the nucleoli and cytoplasm during the cell cycle. Under normal condition, NPM located in the nucleoli, but a small amount is present in the nucleoplasm (FIG. 2B, left). BCL2-associated X protein (BAX), a mitochondria mediated apoptosis protein, is mainly located in the nucleoplasm, but a small amount is present in the cytosol (FIG. 1C, left).

In response to cell stress (e.g., UV radiation or contacting with anti-cancer agents), NPM is translocated from the nucleolus to nucleoplasm (FIG. 2B, middle panel) and cytosol (FIG. 2B, right panel), and bound to BAX. Without being bound by any particular theory, it is believed that the binding of NPM to BAX in the cytosol effectively blocks mitochondrial translocation, oligomerization and activation of BAX, thereby rendering cells resistant to cell death (see death evasion pathway in FIG. 2).

By inhibiting NPM expression, cytosolic BAX is translocated to mitochondria and targeted the mitochondrial inner membrane, where BAX is oligomerized. The mitochondria forms pores, loses membrane potential, releases cytochrome C into cytoplasm, and activates cascades for apoptosis (see apoptosis pathway in FIG. 2).

The present compositions and methods can be used to treat or inhibit the growth of any type of cancer. In some embodiments, the cancer to be treated or the cancer growth to be inhibited is a solid or hematological tumor, such as, for example, liver, bile duct, breast, lung, gastric, pancreatic, colorectal, uterus, cervical cancer, leukemias and lymphomas.

Treatment may be administered alone, or as an adjuvant to surgery, e.g., before surgery to reduce the tumor size and/or following surgery to reduce the possibility of metastases, e.g., by inhibition of the growth and migration of circulating tumor cells through the blood stream.

The NPM inhibitor can be administered before, after or simultaneously with the anti-cancer agent.

In certain instances, the therapy includes a combination of anti-cancer agents to be administered together with an NPM inhibitor.

The following examples further illustrate the present invention. These examples are intended merely to be illustrative of the present invention and are not to be construed as being limiting.

Material and Methods

1. Preparation of Cancer Cells, NPM Expression Inhibitors and Transfection

Human hepatocarcinoma (HCC) lines, HepG2 (wild-type p53), Hep3B (null-genotype p53), Huh7 (C200Y mutated p53), Mahlavu (S249R mutated p53), colorectal cancer cell line HCT-116, ovarian cancer cell lines SKOV3 and MDAH2774, lung cancer cell line A549, cervical cancer cell line HeLa and breast cancer cell line MCF7 were obtained from American Type Culture Collection (Manassas, Va.). Gastric carcinoma cell line TSGH was purchased from University of California, San Francisco (San Francisco, Calif.), cholaniocarcinoma cell line HuCCT-1 was purchased from JCRB cell bank and uterus cancer cell line Ishikawa was purchased from Sigma-Aldrich (Switzerland).

Pre-designed small interference RNAs (siRNAs) targeting NPM (see SEQ ID NOs:2-5) and p53 (siTP53), and siRNAs with scrambled sequences (siNS) were purchased from Ambion, Austin, Tex. In particularly, the siNM used in the study was the Silencer® Select Negative Control #1. Transfection was performed as previously described in Hsieh et al, "Identifying apoptosis-evasion proteins/pathways in human hepatoma cells via induction of cellular hormesis by UV irradiation." J Proteome Res 2009; 8:3977-3986.

NPM inhibitor NSC348884 was purchased from Santa-Cruz Biotechnology (Santa Cruz, Calif.) and Gambogic acid was purchased from and Enzo Life Siences (Farmingdale, N.Y.).

2. UV Irradiation, Drug Treatments, and Cell Survival/Viability Assays

In Example 1, $1 \times 10^4$ cancer cells were seeded into each well of a 96-well plate followed by transfection with siRNAs in Example 1. Forty-eight hours after transfection, cells at 90% confluence were treated with (50 mJ/cm$^2$) of UV-B (290-320 nm) or one of the following chemotherapeutic agents: Mitomycin C (Kyowa Hakko Kogyo Co., Ltd.), cisplatin (Bristol-Myers Squibb S.R.L.) or doxorubicin (Pfizer Italia S.R.L.). Target cancer therapy, such as Sorafenib (kindly provided by Bayer HealthCare, German) and Lapatinib (purchased from GlaxoSmithKline plc) were prepared in DMSO. Solvent was added to untreated HCC cells as control in each experiment. Cell viability was assessed at 24 h to 48 h after treatment.

For UV irradiation group, cell viability/survival was determined by XTT assay (Roche Applied Science, Mannheim, Germany) 24 h after the exposure to 30, 65, or 100 mJ/cm$^2$ of UV-B. The experiments were conducted at least twice in triplicate and the mean of each dose was used to calculate the half maximal inhibitory concentration ($IC_{50}$).

In Example 6, $2 \times 10^4$ cancer cells were seeded into each well of a 24-well plate, cultured overnight followed by combination drug treatment. IC50, IC90, cell viability and Combination Index were assessed 72 hours after exposure.

3. In Situ Proximity Ligation Assays and Co-Immunoprecipitation

Anti-NPM mouse monoclonal antibody and anti-BAX rabbit polyclonal antibody or anti-actin rabbit polyclonal antibody (negative control) were used as primary antibodies and anti-mouse and anti-rabbit antibodies coupled with short complementing DNA strands were used as secondary antibodies. Ligation of the DNA strands to a circularized oligo in case of direct contact between NPM and BAX, and the subsequent rolling circle amplification incorporating labeled nucleotides was performed using the Duolink II kit (Olink Bioscience, Uppsala, SWE) according to the manufacturer's instruction. After being washed and counterstained with DAPI (4',6-diamidino-2-phenylindole, a fluorescent stain for DNA), the slides were mounted and inspected under the fluorescence microscope.

Cells were grown in a 10 cm plate for co-immunoprecipitation (co-IP). 500 iul of co-IP lysis buffer (50 mM Tris-HCl, 150 mM NaCl, 1 mM EDTA, 1% TritonX-100, pH7.4, 1 mM PMSF, 1 mM Na3VO4, 1 ug/ml aprotinin) was added while the culture dish was placed on ice. Cells were scraped and then lyzed by gentle rocking on ice for 15 minutes. Cellular lysate was centrifuged for 5 min at 12000 g at 4° C. to remove debris. The supernatant was collected in a fresh tube and 2 ug of the first antibody against either NPM or BAX was added. The reaction mixture was rocked gently overnight at 4° C., and followed by the addition of 20 ul of 50% slurry of protein A-sepharose beads. The resultant mixture was incubated at 4° C. for 2 hours followed by centrifugation at 6000 g for 5 min at 4° C. The supernatant was kept as IP efficiency control, while the beads were washed three times with a buffer (10 mM Tris-HCl, 500 mM NaCl, pH 7.4) and heated in 50 ul of 2×SDS loading buffer at 95° C. for 10 minutes, followed by immunoblotting with the identified antibodies as described above.

4. Patients and Tissue Samples

The Internal Review Board for Medical Ethics of Chang Gung Memorial Hospital in Taiwan approved the specimen collection procedures. HCC and its surrounding tissues, as well as the related clinical data from 90 HCC patients were obtained from the Taiwan Liver Cancer Network (TLCN). All HCC tissues were examined and the two core samples from most representative areas in the tissue samples were selected for the tissue microarray blocks. Two core samples were selected from different areas of each HCC tissues.

The ImmunoHistoChemistry (IHC) scores were determined by two independent observers. If there was disagreement between the two observers, the slides were re-examined and a consensus was reached by the observers. IHS Score 0 indicates negative result, 1 indicates weakly positive result, 2 indicates positive result and 3 indicates strongly positive result.

The combined effect of the drugs was analyzed and expressed as Combination Index (CI), using the method of T. C. Chou: Theoretical Basis, Experimental Design, and Computerized Simulation of Synergism and Antagonism in Drug Combination Studies, Pharmacological Reviews. 2006; 58(3):621-81, the entire disclosure of which is incorporated herein by reference. CI between 0.3-0.7 indicates synergism, 0.7-0.85 indicates moderate synergism, 0.85-0.9 indicates slight synergism, 0.9-1.1 indicates additive, 1.1-1.2 indicates slight antagonism, 1.2-1.45 indicates moderate antagonism and 1.45-3.3 indicates antagonism.

Tumor staging was determined in accordance with tumor-node-metastasis (TNM) staging system, as suggested by the American Joint Committee on Cancer/International Union Against Cancer.

The Chi-square test and Fishers Exact test were used for comparison between variables. Kaplan-Meier analysis and the log-rank test were used to illustrate recurrence-free and overall survival probability after patients received primary curative hepatectomy.

Example 1

In-Vitro Evaluation of NPM Inhibitor and Anti-Cancer Agents Combination in HCC

HCC cell lines with different p53 backgrounds, including HepG2 (wild-type p53), Huh7 (C200Y mutated p53), Mahlavu (R249S mutant p53), and Hep3B (deleted p53) were used in this study.

Figure 3:
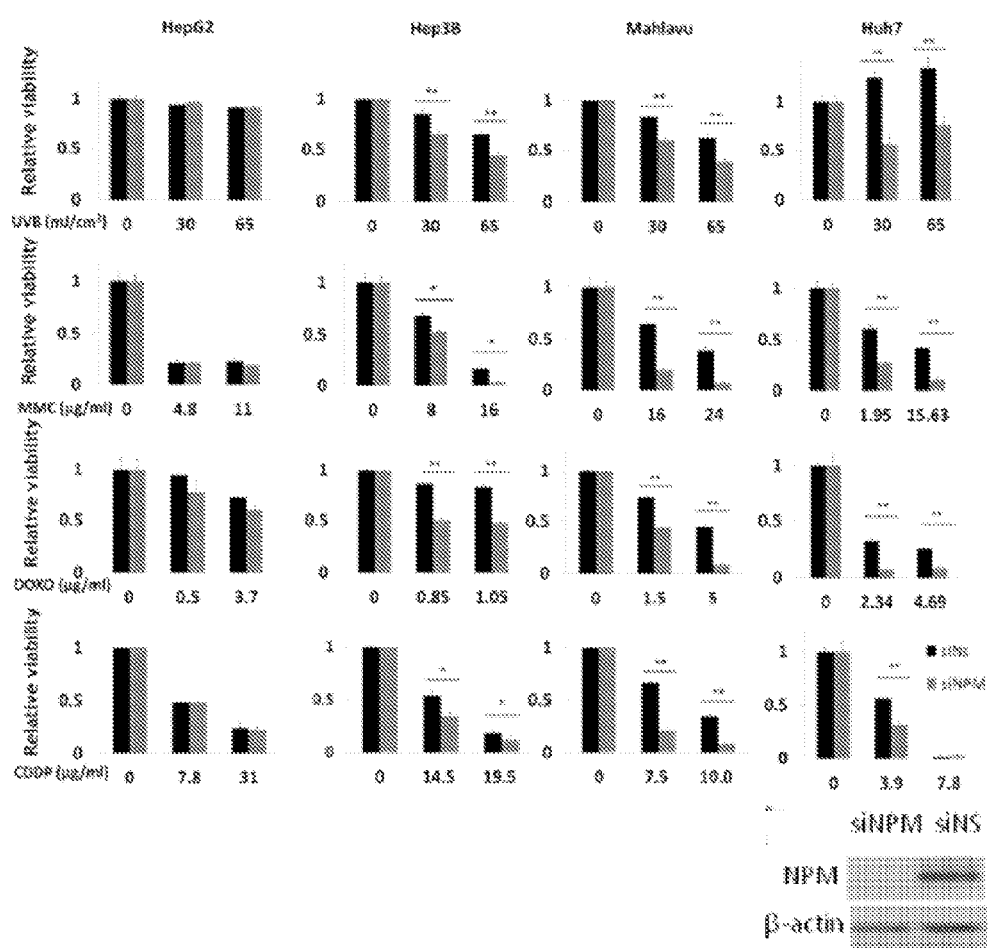
FIG. 3 shows the effect of siNS (siRNA containing scrambled sequences) and siNPM (siRNA inhibits NPM expression) on liver cancer cells with or without treatment with UV radiation (UVB), mitomycin C (MMC), doxorubicin (DOXO) or cisplatin (CDDP).

Referring to FIG. 3, the doses for UVB, MMC, DOXO and CODP at 0 mJ/cm$^2$ or mg/ml indicate HCC cells were not treated with UV-B or conventional chemotherapeutic agents. The siNPM (siRNA inhibiting NPM expression) bars represents groups without UV-B or chemotherapeutic agent treatment but with NPM suppression. The siNS bars represent groups without UV-B, chemotherapeutic agent treatment or NPM suppression. Inhibition of NPM expression by siNPM was confirmed by immunoblotting (FIG. 3, right lower panel).

HCC cells were treated with UV-B or one of the conventional chemotherapeutic agents when the doses for UVB, MMC, DOXO and CODP are above 0 mJ/cm$^2$ or ug/ml. In this group, the siNs bars represent groups without NPM expression inhibition, but were treated with UV-B or conventional chemotherapeutic agents. The siNPM bars groups with NPM suppression and treatment with a chemotherapeutic agent or UV-B radiation. Cell viability was measured by XTT assay. * ($p<0.05$) and ** ($p<0.01$) indicate statistical significance between cells transfected with siNPM and with siNS.

NPM expression inhibition in combination with chemotherapy or UV-B treatment significantly reduced cell viability of HCC cells compare to NPM expression inhibition alone. The results show that the combination of NPM expression inhibition and chemotherapy or UV-B treatment is effective in HCC treatment.

Figure 7:
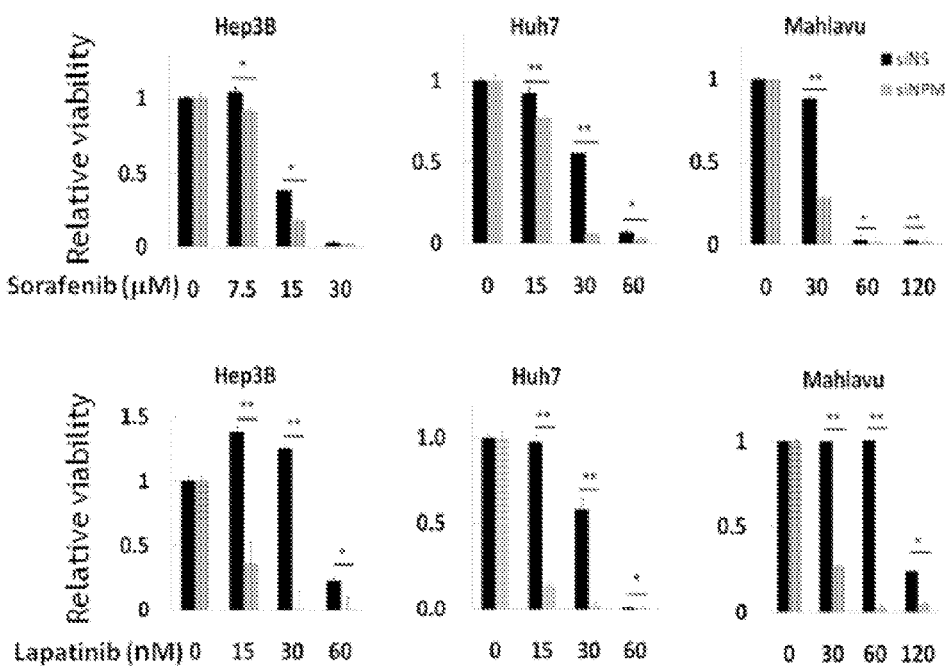
FIG. 7 shows effect of siNS and siNPM on liver cancer cells (Hep3B, Huh7 and Mahlavu) treated with or without target cancer therapies (Sorafenib and Lapatinib).

Referring to FIG. 7, the doses for sorefenib and lapatinib at 0 uM or nM indicate HCC cells were not treated with target cancer therapy. At 0 uM or nM, the siNS (black) bars represent no NPM expression inhibition and no target cancer therapy (control group), while the siNPM (grey) bars represent groups with NPM expression inhibition, but without target cancer therapy.

The doses for sorefenib and lapatinib above 0 uM or nM indicate HCC cells were treated with target cancer therapy. siNS (black) bars with sorefenib and lapatinib doses above 0 uM or nM represent groups without NPM expression inhibition, but were treated with target cancer therapy, whereas siNPM (grey) bars with sorefenib and lapatinib doses above 0 uM or nM represent groups with NPM expression inhibition and treated with target cancer therapy.

Inhibiting NPM expression in combination with target cancer therapy significantly enhanced the cellular susceptibility in Huh7, Hep3B and Mahlavu cells compare to NPM expression suppression or target cancer therapy alone. The results show that the combination of NPM expression suppression and target cancer therapy provide synergistic effect in HCC treatment.

Figure 4:
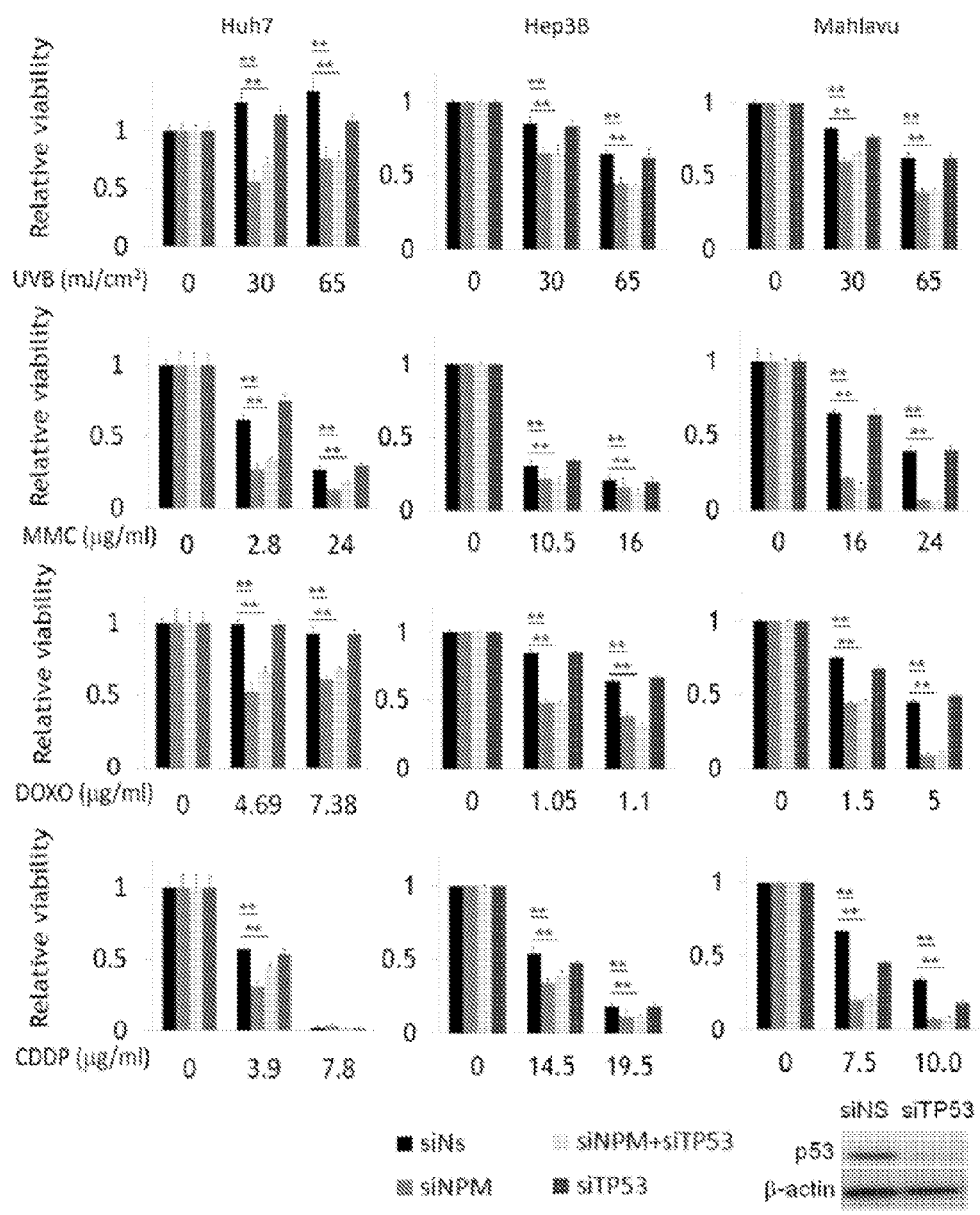
FIG. 4 shows the effect of siNS (siRNA containing scrambled sequences), siNPM (siRNA inhibiting NPM expression), siTP53 (siRNA targeting p53) and the combination of siNPM and siTP53 on liver cancer cells with or without treatment with UVB, MMC, DOXO or CDDP.

The role of p53 in death evasion orchestrated by NPM in cancer cells was further evaluated. The expression of NPM, p53, or simultaneously NPM and p53 were silenced by siNPM and siTP53 (FIG. 4). Silencing of p53 expression alone did not significantly change the sensitivity of the treatments in Huh7, Hep3B, and Mahlavu cells (FIG. 4, siTP53 vs. siNS). Simultaneous silencing of p53 and NPM did not further alter the sensitizing effect exerted by silencing of NPM alone [FIG. 4, siNPM/siNS vs. (siNPM+siTP53)/siNS]. NPM apparently executes its death-evasion activity independently of p53. These findings are of great clinical significance, since p53 mutations are found in more than half of human cancers including HCC, especially in advanced stage HCC.

Example 2

Induction of NPM and BAX Expression by Cellular Stresses

Now referring to FIG. 1A, NPM was upregulated in Huh7, Hep3B, and Mahlavu cells following UV-B (50 mJ/cm$^2$), cisplatin [5.5, 69, and 6.4 µg/ml for Hep3B (3B), HepG2 (G2) and Mahlavu (ML), respectively], and doxorubicin [1.4, 8.8, and 5 µg/ml for Hep3B, HepG2 and Mahlavu, respectively] exposure. BAX expression was also increased in all three HCC cell lines following the treatment of UV-B, cisplatin, and doxorubicin. The expression of β-actin was used as the loading control. Simultaneous induction of BAX (pro-apoptosis) and NPM (anti-apoptosis) of cells upon cellular stress represents counteracting mechanisms regulating apoptosis versus survival response.

Example 3

Nucleoplasmic and Cytoplasmic Translocation of NPM Following Cellular Stresses

Prior to UV irradiation, NPM was mainly located in the nucleoli and a small amount was present in nucleoplasm (FIG. 1B, left panel), while BAX was primarily located in nucleoplasm and a small amount was located in the cytoplasm (FIG. 1C, left panel). Following UV irradiation, NPM was translocated from nucleoli to nucleoplasm (FIG. 1B, middle), and cytoplasm (FIG. 1B, right panel, indicated by an arrow). On the other hand, BAX was translocated to cytosol and accumulated in the mitochondria, particularly in cells undergo apoptosis (FIG. 1C, right panel; indicated by arrows).

Following the suppression of NPM expression by siRNA, HCC cells with relatively low NPM expression have more BAX aggregated in the mitochondria and were found to be more prone to apoptosis, whereas cells with relatively high NPM level have less mitochondrial BAX accumulation and were found to be more resistance to apoptosis. These findings suggest that the anti-apoptosis activity of NPM involves the blockade of BAX mitochondrial translocation.

Example 4

Blockade of BAX Mitochondria Translocation and Oligomerization by NPM

Figure 6:
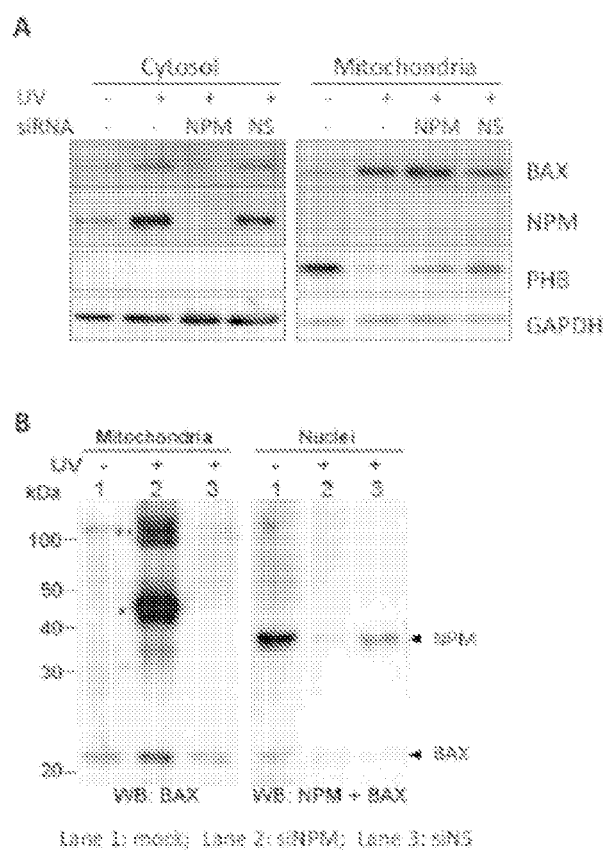
FIG. 6 shows NPM expression blocks the mitochondrial translocation and oligomerization of BAX in liver cancer cells following UV irradiation.

FIG. 6A illustrates cytoplasmic NPM increased after UV irradiation, whereas BAX increased in the cytosol and mitochondria after UV irradiation. Suppressing NPM expression by siRNA reduced the cytosolic BAX, while mitochondrial BAX level increased. This suggests BAX mitochondrial translocation was blocked by NPM in response to cellular stress such as UV treatment. Prohibitin (PHB) and glyceraldehyde 3-phosphate dehydrogenase (GAPDH) were used as the markers for mitochondrial and cytosolic components, respectively. Similar result for mitochondrial BAX enhancement was observed by inhibiting NPM with chemotherapeutic agents, such as staurosporin in Hep3B and Mahlavu cells.

A non-reducing condition for preparing cellular proteins was employed to validate the above findings. Inhibiting NPM expression (FIG. 6B, lane 2) greatly increased the dimmers and oligomers of mitochondrial BAX following UV irradiation, whereas the BAX dimmers and oligomers were barely detected in the mitochondria before UV irradiation (FIG. 6B, lane 1) or without NPM expression inhibition (FIG. 6B, lane 3). In conclusion, NPM blocks the mitochondrial translocation and oligomerization of BAX in HCC cells.

Example 5

Figure 5:
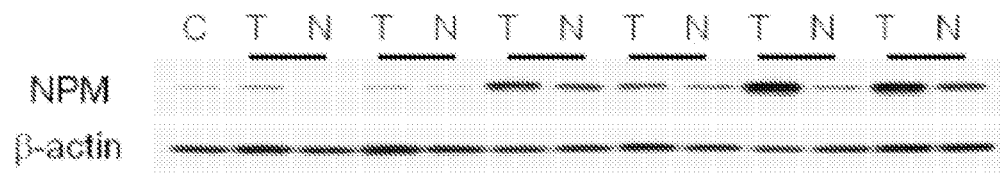
FIG. 5 shows NPM expression in normal liver cells (C), liver cancer cells (T) and para-liver cancer cells (N).

Upregulation of NPM in Human HCC was Associated with Hepatitis B, Portal Vein Invasion, High Recurrence and Poor Prognosis Using immunoblotting assay, NPM level was found to be high in 4 out of 6 HCC samples compared to the matched para-HCC liver tissues and a normal liver tissue (FIG. 5).

The expression of NPM in 90 pairs of HCC and para-HCC liver samples were examined. Overexpression of NPM was found in 38.9% (35/90) of HCC samples and strongly associated with chronic hepatitis B (p<0.0001), advanced cancer stages (p=0.0015), portal vein invasion (p<0.001), tumor recurrence (p=0.0148), and poor overall survival (p=0.0229). See Tables 1-4. NPM upregulation is associated with higher tumor recurrence and lower overall survival, as demonstrated via Kaplan-Meier analyses and log-rank test.

TABLE 1

Correlation of NPM expression to clinical manifestations of patients with HCC

| | | IHC score | | statistics | |
|---|---|---|---|---|---|
| | | 0 | >0 | p | test |
| Etiology | HBV | 18 | 27 | <0.001 | Fisher's exact |
| | HCV | 37 | 8 | | |
| Age* | mean ± SEM | 59.3 ± 3.8 | 56.8 ± 3.6 | 0.539 | Student's t |
| Gender* | male | 12 | 16 | 0.428 | Fisher's exact |
| | female | 6 | 11 | | |
| Cirrhosis* | yes | 10 | 22 | 0.146 | Fisher's exact |
| | no | 8 | 5 | | |
| AFP* | >400 | 12 | 19 | 0.724 | Fisher's exact |
| | <400 | 6 | 8 | | |
| Tumor stage* | I | 6 | 9 | 0.0015 | Spearman correlation |
| | II | 9 | 6 | | |
| | III | 3 | 12 | | |
| Vascular invasion* | yes | 2 | 23 | <0.001 | Fisher's exact |
| | no | 16 | 4 | | |
| Recurrence* | | | | 0.0148 | Log rank |
| Overall survival* | | 0 vs. >0 | | 0.1101 | Log rank |
| | | 0, 1, 2 vs. 3 | | 0.0229 | Log rank[b] |

A total of 90 cases with HCC including 45 cases with chronic hepatitis B and 45 cases with chronic hepatitis C were included and assayed on tissue arrays by immunohistochemistry (IHC)
IHC scores were determined by two independent pathologists.
IHC score: 0, negative; 1, weakly positive; 2, positive; 3, strongly positive
HBV: chronic hepatitis B; HVC: chronic hepatitis C
*Only the 45 cases with HBV-related HCC were included for analyses.

TABLE 2

Immunohistochemistry scores for NPM expression in 45 pairs of hepatitis B-related HCC and non-HCC liver tissues on tissue arrays.

| | IHC score 0 | IHC score 1 | IHC score 2 | IHC score 3 | subtotal |
|---|---|---|---|---|---|
| Stage I | 6 | 5 | 2 | 2 | 15 |
| Stage II | 9 | 0 | 6 | 0 | 15 |
| Stage III | 3 | 5 | 1 | 6 | 15 |
| subtotal | 18 | 10 | 9 | 8 | 45 |

TABLE 3

Immunohistochemistry scores for NPM expression in 45 pairs of hepatitis C-related HCC and non-HCC liver tissues on tissue arrays.

| | IHC score 0 | IHC score 1 | IHC score 2 | IHC score 3 | subtotal |
|---|---|---|---|---|---|
| Stage I | 11 | 3 | 1 | 0 | 15 |
| Stage II | 12 | 0 | 2 | 1 | 15 |
| Stage III | 14 | 1 | 0 | 0 | 15 |
| subtotal | 37 | 4 | 3 | 1 | 45 |

TABLE 4

Correlation of NPM expression to clinical manifestations of patients with HCC

| | IHC score | P value |
|---|---|---|
| HBV vs HCV | 0, 1, 2, 3 | <0.0001[a] |
| | 0 vs. 1, 2, 3 | 0.0001 |
| | 0, 1 vs. 2, 3 | 0.0028 |
| | 0, 1, 2 vs. 3 | 0.03 |
| Stages (HBV only) | 0, 1, 2, 3 | 0.0015[b] |
| | 0 vs, 1, 2, 3 | 0.0821 |

TABLE 4-continued

Correlation of NPM expression to clinical manifestations of patients with HCC

|  | IHC score | P value |
|---|---|---|
|  | 0, 1 vs. 2, 3 | 0.5159 |
|  | 0, 1, 2 vs. 3 | 0.0174 |
| Portal-vein invasion | 0 vs. 1, 2, 3 | 0.0019 |
| (HBV only) | 0, 1, 2 vs. 3 | 0.0075 |
| Disease-free survival | 0 vs. 1, 2, 3 | 0.0148[c] |
| (HBV only) | 0, 1, 2 vs. 3 | 0.1193[c] |
| Overall survival | 0 vs. 1, 2, 3 | 0.1101[c] |
| (HBV only) | 0, 1, 2 vs. 3 | 0.0229[c] |

HBV = Chronic Hepatitis B;
HCV = Chronic Hepatitis C;
[a]Kruskal-Wallis test;
[b]Spearman correlation = 0.229;
[c]Log-rank test.

Example 6

In-Vitro Evaluation of NPM Inhibitor and Anti-Cancer Agent Combination in Various Cancer Cell Lines Combinations of NPM inhibitor and an anti-cancer agent were evaluated in the following cancer cell lines: HCC cell lines (Huh7 and Mahlavu), gastric carcinoma cell line (TSGH), cholangiocarcinoma cell line (HuCCT-1), colorectal carcinoma cell line (HCT-116), ovarian cancer cell lines (SKOV3 and MDAH2774), lung cancer cell (A549), uterine cancer cell line (Ishikawa), cervical cancer cell line (HeLa) and breast cancer cell line (MCF7).

As shown in Table 5, the overall effect of Sorafenib (an anti-cancer agent) and NPM inhibitor (NSC348884 or Gambogic acid) combination on HCC cell line indicates additivity to synergy.

TABLE 5

The effect of Sorafenib in combination with NSC348884 or Gambogic acid on HCC.

| | | Combination Indices (CI) | | | |
|---|---|---|---|---|---|
| Drug (Molar Ratio) | Cell line | 50% Effective Dose | 75% Effective Dose | 90% Effective Dose | Overall result |
| Sorafenib + NSC348884 (1:1) | Huh7 | 1.08 | 1.06 | 1.18 | Additive |
| Sorafenib + Gambogic acid (1:2) | Huh7 | 0.52 | 0.68 | 1.01 | Synergism at 50% and 75%, additive at 90% |
| Sorafenib + Gambogic acid (2:1) | Mahlavu | 0.72 | 0.83 | 0.96 | Synergism at 50% and 75%, additive at 90% |

The effect of Lapatinib (an anti-cancer agent) and Gambogic acid (an NPM inhibitor) combination on eight different cancer cell lines are summarized in Table 6. Taken as a whole, the results of all cancer cell lines indicate additivity to synergy.

TABLE 6

The effect of Lapatinib in combination with Gambogic acid on various cancer cell lines.

| | | Combination Indices (CI) | | | |
|---|---|---|---|---|---|
| Lapatinib:Gambogic Acid Molar Ratio | Cancer Cell line (Origin) | 50% Effective Dose | 75% Effective Dose | 90% Effective Dose | Overall result |
| 15:2 | Huh7 (HCC) | 0.84 | 0.88 | 1.05 | Synergism at 50% and 75%; additive at 90% |
| 2:1 | Mahlavu (HCC) | 0.67 | 0.75 | 0.85 | Synergism |
| 15:2 | TSGH (Gastric) | 0.94 | 0.90 | 0.87 | Synergism at 90%, additive at 50% and 75% |
| 15:2 | HuCCT-1 (Cholangio Carcinoma) | 0.69 | 0.75 | 0.81 | Synergism |
| 15:2 | HCT-116 (Colorectal) | 0.71 | 0.66 | 0.62 | Synergism |
| 15:2 | SKOV3 (Ovarian) | 0.67 | 0.54 | 0.47 | Synergism |
| 15:1 | MDAH2774 (Ovarian) | 0.89 | 0.89 | 0.93 | Synergism at 50% and 75%, additive at 90% |
| 15:2 | A549 (lung) | 0.97 | 1.02 | 1.01 | Additive |
| 10:1 | Ishikawa (Uterus) | 0.77 | 0.79 | 0.79 | Synergism |
| 2:1 | HeLa (Cervical) | 0.73 | 0.64 | 0.56 | Synergism |
| 15:1 | MCF7 (Breast) | 0.98 | 0.95 | 0.96 | Additive |

The effect of Lapatinib (an anti-cancer agent) and NSC348884 (an NPM inhibitor) combination on eight different cancer cell lines are summarized in Table 7. Taken as a whole, the results of all cancer cell lines indicate mixed additivity/synergy.

TABLE 7

The effect of Lapatinib in combination with NSC348884 on various cancer cell lines.

| | | Combination Indices (CI) | | | |
|---|---|---|---|---|---|
| Lapatinib:NSC348884 Molar Ratio | Cancer Cell line (origin) | 50% Effective Dose | 75% Effective Dose | 90% Effective Dose | Overall result |
| 15:4 | Mahlavu (HCC) | 1.74 | 1.79 | 1.87 | Antagonism |
| 20:3 | TSGH (Gastric) | 0.14 | 0.35 | 0.90 | Synergism |
| 20:3 | HuCCT-1 (Cholangio carcinoma) | — | 0.17 | 0.25 | Synergism |
| 15:2 | HCT-116 (Colorectal) | 0.63 | 0.77 | 0.94 | Synergism |
| 15:4 | SKOV3 (Ovarian) | 0.96 | 0.94 | 0.93 | Additive |
| 5:1 | MDAH2774 (Ovarian) | 0.32 | 0.40 | 0.50 | Synergism |

TABLE 7-continued

The effect of Lapatinib in combination with NSC348884 on various cancer cell lines.

| Lapatinib:NSC348884 Molar Ratio | Cancer Cell line (origin) | Combination Indices (CI) | | | Overall result |
|---|---|---|---|---|---|
| | | 50% Effective Dose | 75% Effective Dose | 90% Effective Dose | |
| 15:2 | A549 (Lung) | 0.91 | 0.91 | 0.95 | Additive |
| 20:1 | Ishikawa (Uterus) | 1.09 | 1.06 | 1.04 | Additive |
| 15:4 | HeLa (Cervical) | 1.65 | 1.71 | 1.77 | Antagonism |
| 5:1 | MCF7 (Breast) | 0.49 | 0.86 | — | Synergism |

These results demonstrate that combination treatment of Lapatinib (an anti-cancer agent) with NSC348884 (an NPM inhibitor) yield additive to synergistic anti-cancer effect in most cancer cell lines, except Mahlavu (HCC) and HeLa (cervical) cell lines.

Referring to Table 8, lower concentrations of Lapatinib and NSC348884 are needed for inhibiting HCC and cervical cancer in combination therapy form than that of monotherapy form. The results indicate Lapatinib and NSC348884 combination is effective in cancer cell inhibition and can be present in a dose that is less than to the dosage normally administered in monotherapy regimen.

TABLE 8

IC50 of Lapatinib and NSC348884 as monotherapy and combination therapy in HCC and cervical cancer cell

| Cancer cell Line (Origin) | IC50 ($\mu$M) | | | |
|---|---|---|---|---|
| | Monotherapy | | Combination Therapy | |
| | Lapatinib | NSC348884 | Lapatinib | NSC348884 |
| Mahlavu (HCC) | 12.83 | 6.15 | 14.4 | 3.84 |
| HeLa (Cervical) | 20.76 | 6.24 | 18.45 | 4.92 |

What is claimed is:

1. A method for reducing or inhibiting cancer cells in a subject, the method comprising the steps of:
   (a) contacting the cancer cells with an NPM inhibitor, wherein the NPM inhibitor is gambogic acid; and
   (b) administering an effective amount of an anti-cancer agent, wherein the anti-cancer agent is target cancer therapy, wherein said target cancer therapy is "sorefenib or lapatinib";
   wherein the cancer cells are selected from the group consisting of hepatocarcinoma, gastric cancer, cholangiocarcinoma, colorectal cancer, ovarian cancer, lung cancer, uterine cancer, and breast cancer, wherein said steps of contacting and administering provide a synergistic effect on reducing or inhibiting said cancer cells in said subject.

2. The method of claim 1, wherein the NPM inhibitor is administered prior to, after or simultaneously with the anti-cancer agent.

3. The method of claim 1, wherein the ratio of the anti-cancer agent to NPM inhibitor is 20:1 to 2:1.

* * * * *